United States Patent
Gardiner et al.

(10) Patent No.: US 6,348,502 B1
(45) Date of Patent: Feb. 19, 2002

(54) FORMULATIONS FOR THE TREATMENT OF GASTRO-OESOPHAGEAL REFLUX

(75) Inventors: Fiona Kate Gardiner, Trelex sur Nyon (CH); Ian Gordon Jolliffe, Cottingham; Peter William Dettmar, Patrington, both of (GB)

(73) Assignee: Reckitt & Colman Products Limited, Slough (GB)

( * ) Notice: Subject to any disclaimer, the term of this patent is extended or adjusted under 35 U.S.C. 154(b) by 0 days.

(21) Appl. No.: 09/719,129

(22) PCT Filed: Jun. 1, 1999

(86) PCT No.: PCT/GB99/01717

§ 371 Date: Apr. 4, 2001

§ 102(e) Date: Apr. 4, 2001

(87) PCT Pub. No.: WO99/63986

PCT Pub. Date: Dec. 16, 1999

(30) Foreign Application Priority Data

Jun. 10, 1998 (GB) .............................................. 9812426

(51) Int. Cl.⁷ .............................................. A61K 31/16
(52) U.S. Cl. ....................................................... 514/627
(58) Field of Search ......................................... 514/627

(56) References Cited

U.S. PATENT DOCUMENTS

| 4,284,657 A | 8/1981 | Stanton ....................... 426/651 |
| 5,431,914 A | 7/1995 | Adekunle et al. ........... 424/401 |
| 5,536,506 A | 7/1996 | Majeed et al. ............... 424/464 |

FOREIGN PATENT DOCUMENTS

| EP | 0 241 804 A2 | 3/1987 | .......... A61K/33/10 |
| EP | 0 709 098 A1 | 5/1996 | .......... A61K/45/06 |
| GB | 1 524 740 | 9/1978 | ......... A61K/31/715 |
| GB | 2 222 772 A | 3/1990 | .......... A61K/31/34 |
| GB | 2 298 365 A | 9/1996 | ............ A61K/9/08 |
| WO | WO98/56356 | 12/1988 | ............ A61K/9/16 |
| WO | WO96/40079 | 12/1996 | ............ A61K/9/24 |

OTHER PUBLICATIONS

"Chili Protects against Aspirin–Induced Gastroduodenal Mucosal Injury in Humans", Digestive Diseases and Sciences 1995, 40(3), 580–583, (K.G. Yeoh et al.) (whole document).
"Capsaicin–Sensitive Nerves Mediate Esophageal Mucosal Protection", Surgery, Aug. 1991, 419–426 (B.L. Bass et al.).
Copy of GB Search Report for GB application No. 9812426.6 dated Sep. 10, 1998.
Patent Abstracts of Japan, vol. 007, No. 285 (C–201), Dec. 20, 1983 & JP 58 162520 A (Seisan Kaihatsu Kagaku Kenkyusho), Sep. 27, 1983.
"Capsaicin and the stomach. A review of experimental and clinical data", Journal of Physiology (Paris), vol. 91, No. 3–5, May 1997, XP002115080, abstract.
Copy of PCT International Search Report for PCT/GB99/071717 dated Sep. 27, 1999.
Caplus Abstract No. 1990–578281 & JP 020078613 A (Taisho) (1990).
Copy of GB Search Report for GB application No. 9912509.8 dated Sep. 27, 1999.

*Primary Examiner*—Raymond Henley, III
(74) *Attorney, Agent, or Firm*—Fish & Richardson P.C.

(57) ABSTRACT

Formulations for the treatment of gastro-oesophageal reflux diseases include a carrier vehicle and an active gastro-protective agent. The carrier vehicle is either capable of forming a floating barrier layer on contact with gastric acid or of forming a bioadhesive film before any contact with gastric acid, so as to protect gastric mucosa from irritation by the gastric acid. A preferred active ingredient is capsaicin. The carrier vehicle preferably contains alginate or cross-linked polyacrylic acid.

23 Claims, No Drawings

FORMULATIONS FOR THE TREATMENT OF GASTRO-OESOPHAGEAL REFLUX

This is a 371 of PCT/GB99/01717 filed Jun. 1, 1999.

BACKGROUND OF THE INVENTION

The present invention relates to pharmaceutical compositions suitable for oral delivery and, in particular, to pharmaceutical compositions for the treatment of reflux oesophagitis, gastritis, dyspepsia or peptic ulceration, or for use as sustained release or targeted delivery compositions.

Reflux oesophagitis occurs when small amounts of gastric juices, food and/or bile acids pass into the lower part of the oesophagus and cause oesophageal inflammation (oesophagitis) accompanied by pain which may manifest itself in the form of heartburn.

One approach to the problem of reflux oesophagitis has been to administer a preparation which, on contact with gastric acid, generates a carbonated gelatinous foam or raft which floats on the stomach contents. When gastric reflux occurs, this raft precedes the stomach contents into the oesophagus, thus protecting the mucosa from further irritation.

Known preparations of this type include solid preparations in the form of powder or tablets containing alginic acid, sodium bicarbonate and antacid materials; or liquid preparations containing sodium alginate, sodium bicarbonate and calcium carbonate which are marketed under the name of GAVISCON (Registered Trade Mark—Reckitt & Colman Products Ltd). In our British Patent No. 1524740 we describe such preparations, which are in liquid form.

Suppressants of gastric acid secretion are known to increase the healing of gastric ulcers and the effect of capsaicin and/or cimetidine on gastric acid secretion was therefore investigated in a recent study. It was found that capsaicin protects the gastric mucosa against experimental injury, such as acetic-acid induced gastric ulceration in rats (J. Y. Kang, C. H. Teng and F. C. Chen; Gut 1996, 38, 832).

The capsaicin and/or cimetidine was introduced directly into an ex vivo chamber prepared by surgery in order to establish the efficacy of the treatment. The effect of capsaicin on the healing of such gastric ulcers was compared with the effects of cimetidine (a histamine 2-receptor antagonist) which is widely used for the treatment of peptic ulcers, and with a combination of cimetidine and capsaicin.

It was concluded that capsaicin promotes the healing of acetic-acid induced gastric ulcers, but that this effect is blunted by the prior administration of cimetidine. In addition, it appears that capsaicin has no effect on gastric acid secretion.

It has also been established that capsaicin provides mucosal protection in white rabbits against topical injury by noxious agents such as ethanol (B. L. Bass, K. S. Trad, J. W. Harman and F. Z. Hakki; Surgery August 1991, 419). The capsaicin was administered directly to the white rabbits at the gastro-oesophageal junction via cannulae and the blood flow was monitored through catheters positioned in the left ventricle and iliac artery.

It is believed that mucosal protection arises because capsaicin stimulates the chemosensitive afferent neurones of the mucosa and submucosa, thereby causing local release of vasoactive and permeability-altering peptides resulting in increased blood flow. The specific protective factors associated with augmentation of blood flow remain unknown however.

Further studies have indicated that chilli has a protective effect on acute aspirin-induced gastroduodenal mucosal injury in humans (K. G. Yeoh, J. Y. Kang, I. Yap, R. Guan, C. C. Tan, A. Wee and C. H. Teng; Diseases and Sciences 1995, 40(3), 580).

Healthy volunteers took 20 g of chill powder (containing 9.56 mg of capsaicin) orally with 200 mls of water, followed by 600 mg of asprin with 200 mls of water. The resulting lesions were observed by gastroduodenoscopy both in this group and in a control group.

The chilli powder exhibited a gastroprotective effect against aspirin-induced injury. The mechanism of action is unclear, but is thought to be due to increased gastric mucosal blood flow.

Capsaicin-sensitive nerves contribute to the maintenance of tissue integrity, and also influence healing of acute and chronic lesions. Ablation of capsaicin-sensitive nerves increases the degree of gastric lesions induced by a number of mechanical and chemical stimuli, including NSAIDs, alcohol and acid. In contrast, intragastric administration of a low concentration of capsaicin appears to protect the gastric mucosa against these agents and aids lesion-healing.

The efficacy of capsaicin has been explained by the local release of neuoropeptides from afferent nerve endings, such as Substance P, CGRP and sonatostatin, which in turn acts to increase local blood flow. In vivo, capsaicin-sensitive neurones are suggested to be stimulated by the reduction in pH presented to the gastric mucosa, which signifies an injurious situation. Similarly, stimulation of capsaicin-sensitive neurones by both acid and capsaicin in rats has been shown to increase duodenal bicarbonate secretion (Inada and Satoh). Thus, capsaicin may act to support natural defensive pathways both prophylactically, and in the face of injury.

However, for the general treatment of gastric disorders in patients the administration of capsaicin by any of the above methods is unsuitable and could not be used as a means of treating the general population. The prior art treatments are particularly unsuitable for use in human patients and do not allow for selective treatment of the affected area using an acceptable dosage form. Indeed, it is probable that patients may be unwilling or unable to consume a large amount of chilli orally in the manner suggested by Yeoh et al.

The prior art thus does not disclose a generally applicable method of administering capsaicin to patients, nor does it provide a suitable vehicle for the administration of capsaicin to the oesophageal region. Thus, there remains a need for an active agent which can be delivered to the oesophageal region and hence for a suitable vehicle for the active agent. In the case of the present invention, the active agent can be directed to the oesophaagus to provide relief from oesophageal inflammation and lesions, such as those sustained during periods of heartburn and indigestion. Alternatively, it can function as a prophylactic prior to the addition of agents likely to be harmful to the gastric mucosa, for example asprin, perhaps after damage due to overindulgence of alcohol.

Ideally, the active ingredient should be delivered to the site of sensitive neurones located throughout the gastrointestinal tract (including the oesophagus and stomach) which provide a gastroprotective function and which are sensitive to capsaicin and other gastroprotective agents.

SUMMARY OF THE INVENTION

According to the present invention, there is provided a pharmaceutical composition for the treatment of gastro-oesophageal reflux disease which comprises a carrier vehicle which is capable of producing a floating barrier layer on contact with gastric acid, or is capable of forming a bioadhesive film which binds to the oesophageal region and at least one active ingredient which is selected from capsaicin ((E)-(N)-[(4-hydroxy-3-methoxphenyl)-methyl]-8-methyl-6-nonenamide), zingerone (4-(4-hydroxy-3-methoxyphenyl)-2-butanone),curcumin (1,7-bis(4-hydroxy-3-methoxyphenyl)-1,6-heptadiene-3,5-dione), piperine (1-[5-1,3-benzodioxol-5-yl)-1-oxo-2,4-pentadienyl] piperidine), resiniferatoxin (daphnetoxin 6,7-deepoxy-6,7-didehydro-5-deoxy-21-dephenyl-21-(phenylmethyl)-20-(4-hydroxy-3-methoxybenzeneacetate), pharmaceutically acceptable derivatives and salts thereof.

For the purposes of the present invention, gastro-oesophageal reflux disease includes reflux oesophagitis, gastritis, dyspepsia, peptic ulceration and/or Barrett's oesophagus.

DETAILED DISCLOSURE

Thus it will be seen that protection of the oesophageal region in accordance with the invention by delivering the required dosage to the required site can be achieved in two ways. The oesophagus can be protected by coating on reflux with the carrier vehicle which has formed a carbonated raft, mucoadhesive granules or an oil or wax film, following contact with gastric acid. In this case, the formulation is such that a carbonated raft or an oily or wax film forms a barrier layer on reaching the stomach. The barrier layer floats on the surface of the gastric acid and thus contacts the oesophagus before any gastric acid is able to do so. The oil may also form a barrier layer by coating the oesophagus directly as the oil passes through the upper gastrointestinal tract towards the stomach.

Alternatively, the formation of a bioadhesive film following ingestion of the formulation and prior to contact with gastric acid will serve to protect the oesophagus from damage by gastric acid. The bioadhesive film is thus formed on the oesophageal mucosa and prevents contact with acid in the event that gastric reflux occurs. Compounds which will form bioadhesive films include crosslinked polyacrylic acid, also known as carbomer (sold as Carbopol (Registered Trade Mark of Goodrich), alginic acid or alginates (such as, for example sold by Pronova Biopolymer asa), xanthan gum, locust bean gum and/or combinations of the above.

Alginate raft-forming products such as Gaviscon (Registered Trade Mark Reckitt & Colman Products Limited) are particularly suitable as a delivery vehicle for the active ingredients of the present invention. This type of delivery vehicle is good at selectively delivering the active ingredient to the required site, maintaining its concentration there and reducing its spread to surrounding tissues.

Preferably, the carrier vehicle includes alginate or pectin, xanthan gum or carrageenan.

In the context of the present invention, the active ingredients include both the crude extracts of and the specific active ingredients of: capsicum, cayenne pepper, black pepper, paprika, mace, mustard, ginger, turmeric and papaya seed.

The pharmaceutical compositions of the invention may comprise one or more active ingredients, together with one or more agents capable of producing a carbonated foam or bioadhesive film.

The pharmaceutical compositions of the present invention may also include one or more pharmaceutically acceptable excipients.

Alginate raft-forming products are particularly suitable as vehicles for the delivery of active ingredients (i.e. locally-acting ulcer-healing agents) to the oesophagus and stomach. Such active ingredients protect and heal the upper gastrointestinal tract, by simulating the body's active defence rechanism. Additional benefits of this regimen include the anti-nausea effect of such a preparation and the feeling of a warming sensation on swallowing which would provide the patient with a psychological boost because the patient can feel it working.

Furthermore, conventional treatments employing proton pump inhibitors are not recommended for long term use because it is suspected that the absence of gastric acid secretion may cause bacterial growth in the stomach. Some workers have even suggested that there is a risk of cancer associated with such long term use of proton pump inhibitors although this is not proven. The formulation of the present invention has the additional advantage of being considerably cheaper than a proton pump inhibitor.

In contrast, the active ingredients in the formulations of the present invention historically have been widely consumed in the form of herbal extracts. Moreover, the mode of action of capsaicin and the other active ingredients is such that they complement the body's natural defences in a positive way by stimulating chemosensitive afferent neurons whereas proton pump inhibitors have, by their nature, an inhibitory effect.

The applicant has found that the incorporation of one or more locally-acting ulcer-healing agents (for example, capsaicin, zingerone, piperine etc. in a preparation which provides a floating barrier layer such as an alginate raft-forming product, or in a polymeric agent capable of forming a bioadhesive film, provides a novel treatment for gastric disorders. Examples of suitable raft-forming products include Gaviscon (Registered Trade Mark), Algicon (Registered Trade Mark), Gastrocoat (Registered Trade Mark), or Magnatol (Registered Trade Mark).

The active ingredient can thus be given orally as part of an alginate containing product which forms a raft on contact with the stomach acids, whereby the active ingredient is delivered to the oesophageal mucosa on reflux. Alternatively, an oral composition capable of forming a bioadhesive film on the gastric mucosa may be administered; this may be in the form of a single formulation or in the form of two separate formulations which form a bioadhesive film in situ after ingestion. In either case, the active ingredient which is contained in the bioadhesive film contacts the mucosa thereby preventing or assisting in preventing the gastric acid from contacting the mucosa and thus protecting the mucosa from further irritation and providing remedial treatment of any gastric lesions present.

Salts of the active ingredient of the composition of the present invention may also provide the desired activity. However, the therapeutic activity generally resides in the moiety derived from the active compound of the formulation and the use of salts thereof is of less importance. Ideally, for therapeutic and prophylactic purposes any salt is pharmaceutically acceptable to the patient. Examples of pharmaceutically acceptable salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example p-toluenesulphonic acids, mannuronic acid, guluronic acid, and polyacrylic acid.

Derivatives of the active ingredient according to the present invention may also provide the desired activity. Derivatives are intended to include structurally related compounds including the active moiety of the active ingredient, for example, dihydrocapsaicin.

The present invention also includes within its scope formulations as defined above, including compounds, derivatives and pharmaceutically acceptable salts thereof, for use in therapy, and particularly in the treatment of gastro-oesophageal reflux disease.

A further aspect of the present invention provides the use of a composition as defined above in the preparation of a medicament for the treatment of gastric ulcers and/or gastritis (inflammation of the gastric mucosa).

Another aspect of the present invention envisages a method of treatment of gastro-oesophageal reflux disease which comprises administration to a patient of a composition as herein before defined.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

When presented in unit dose form the pharmaceutical formulation may contain a predetermined amount of the active ingredient per unit dose. Such a unit may contain for example from 0.001 mg to 10 mg capsaicin, preferably from 0.25 mg to 2.5 mg, depending on the severity of the condition being treated, the nature of the oral formulation and the age, weight and condition of the patient. The dosage administered may ultimately be at the discretion of an attendant physician or may be within a pre-defined range for self-administration by the patient. However, an effective amount of a compound of the present invention for the treatment of gastro-oesophageal reflux disease will generally be in the range of from 0.01 mg to 40 mg per day and more usually will be in the range of from 0.1 mg to 10 mg per day. This amount may be given in a single dose per day or more usually in a number (such as two, three, four, five or six) of sub-doses per day such that the total daily dose is the same. Thus, in the case in which an alginate containing product, for example, Gaviscon (RTM), is used as the delivery vehicle and capsaicin is the active ingredient, a typical regimen may involve a dose of 0.025 mg to 2.5 mg of capsaicin four times per day. The amount of active ingredient contained in the formulation will, of course, depend on the delivery vehicle and on the particular active ingredient. Capsaicin is the most effective active ingredient, and in the case of other active ingredients the dosage appropriate may be 10 or 100 times or more greater than those required when capsaicin is used.

An effective amount of the active ingredient in the case in which the active ingredient is presented as a salt may be determined as a proportion of the effective amount of the free active ingredient per se.

The formulations may be prepared by any method known in the art of pharmacy, for example by bringing into association the active ingredient with the polymeric agent(s), and excipient(s) when present.

The following examples illustrate compositions according to the invention.
(a) Floating Formulations In each of Examples 1 to 5 below, the products float on the stomach contents and release slowly into the stomach contents. If reflux occurs, the oesophagus is then coated with a solution of the active ingredient (capsaicin or resiniferatoxin in the case of Examples 1 to 5) providing a local action for the therapeutic effect.

EXAMPLE 1

Chewable Tablet
Capsicum oleoresin qs to give 2.5 mg capsaicin per tablet

| | |
|---|---|
| Alginic acid | 250 mg |
| Sodium bicarbonate | 85 mg |
| Calcium carbonate | 20 mg |
| Polyvinylpyrrolidone | 50 mg |
| Mannitol | 700 mg |
| Flavours & Sweeteners | qs |
| Magnesium stearate | 30 mg |

The ingredients are mixed, except the flavours and the magnesium stearate. The mixture is then granulated by mixing with isopropanol (200 mls per kg) and dried at 50° C. The granules are sieved and mixed with magnesium stearate and the flavours and sweeteners are then pressed into tablets.

EXAMPLE 2

Liquid
Resiniferatoxin—sufficient to give 2.5 mg of resiniferatoxin

| | |
|---|---|
| Sodium alginate | 500 mg |
| Sodium bicarbonate | 250 mg |
| Calcium carbonate | 150 mg |
| Carbopol 974P (Registered Trade Mark) | 65 mg |
| Methyl parabens | 40 mg |
| Propyl parabens | 6 mg |
| Flavours & sweeteners | qs |
| Water to | 10 ml |

The resiniferatoxin, alginate, bicarbonate, calcium carbonate, preservatives, flavours and sweeteners are dispersed in 40% of the water. The Carbopol is dispersed in 50% of the water and neutralised with sodium hydroxide to give a solution having pH 7.5. The two aqueous mixtures are combined and mixed until homogenous. Water is then added to make up to a volume of 10 mls and the diluted solution is thoroughly mixed to give a homogenous solution.

EXAMPLE 3

Tablet
Capsicum oleoresin fine powder—sufficient to give 2.5 mg of capsaicin

| | |
|---|---|
| Hydroxypropyl methyl cellulose | 200 mg |
| Citric acid | 50 mg |
| Sodium bicarbonate | 100 mg |
| Microcrystalline cellulose | 100 mg |
| Magnesium stearate | 10 mg |

The powders are mixed together until they have become homogenous and the intimate mixture is compressed into tablets.

EXAMPLE 4

Capsule
Capsicum oleoresin fine powder—sufficient to give 2.5 mg of capaicin

| | |
|---|---|
| Dimethicone 350 oil | 250 mg |
| Medium chain triglyceride oil | 250 mg |

The ingredients are mixed together and filled into soft gelatin capsules. The oil containing the capsaicin floats on the stomach contents and coats the oesophagus walls on each occasion there is a reflux episode.

EXAMPLE 5

Capsule
Capsicum oleoresin fine powder—sufficient to give 2.5 mg of capsaicin
Vegetable wax The capsicum is coated with the wax using a spray congealing/coating method to give wax-coated granules. The granules are filled into a hard gelatin capsule which ruptures in the stomach following ingestion. The wax-coated granules are released and float on the gastric contents, releasing the active ingredient.

Oesophagus/Stomach Adhesive Coating Delivery

In each of Examples 6 to 9, the product adheres to the oesophagus and/or stomach lining following oral delivery.

EXAMPLE 6

Liquid
Capsicum oleoresin fine powder—sufficient to give 2.5 mg of capsaicin

| | |
|---|---|
| Carbopol 974P | 100 mg |
| Sodium hydroxide | 37 mg |
| Calcium carbonate | 100 mg |
| Sodium bicarbonate | 100 mg |
| Flavours, sweeteners, preservatives | qs |
| Water to | 10 mls |

The Carbopol is dispersed in 80% of the water and neutralised with sodium hydroxide. The remaining ingredients are dispersed in most of the remaining water and mixed with the Carbopol solution. The mixture is made up to volume with water and mixed until homogenous. On ingestion, the liquid sticks to the oesophagus and to the mucus lining the stomach.

EXAMPLE 7

Chewable Tablet
Resiniferatoxin—sufficient to give 2.5 mg of resiniferatoxin

| | |
|---|---|
| Carbopol 974P | 100 mg |
| Microcrystalline cellulose | 100 mg |
| Calcium carbonate | 100 mg |
| Mannitol | 480 mg |
| Xylitol | 180 mg |
| Flavours, sweeteners | qs |
| Magnesium stearate | 10 mg |

The powders, except magnesium stearate, are mixed together and then granulated using water. The granules of the powder mixture are dried in a fluid bed dryer and the dried granules are sieved and mixed with magnesium stearate. The resulting mixture is pressed into tablets.

EXAMPLE 8

Tablet
Capsicum oleoresin fine powder—sufficient to give 2.5 mg of capsaicin

| | |
|---|---|
| Carbopol 974P | 100 mg |
| Microcrystalline cellulose | 240 mg |
| Sodium hydroxide | 10 mg |
| Croscarmellose sodium | 30 mg |
| Magnesium stearate | 3 mg |

The capsicum, carbopol and Microcrystalline cellulose are mixed together in a high speed mixer granulator. The sodium hydroxide is dissolved in 50 mg of water and the resulting solution is added slowly to the above powder mix while blending. The resulting granules are dried in a fluid bed dryer and the dried granules are subsequently passed through a 1000 $\mu$m screen. The screened dried granules, the croscarmellose sodium and the magnesium stearate are blended together and pressed into tablets.

On administration the tablets disintegrate in the stomach contents to release mucoadhesive granules. The granules slowly release the capsaicin into the stomach contents and, when reflux occurs, the capsaicin is refluxed with the stomach contents to cover the oesophagus.

EXAMPLE 9

Adhesive Microcapsules

The formulation of this example consists of microcapsules of sodium alginate coated with chitosan chloride.
Capsicum oleoresin fine powder—sufficient to give 2.5 mg of capsaicin
Sodium alginate
Chitosan Chloride
Calcium Chloride
Water qs The sodium alginate is dissolved in sufficient water to give a 2% aqueous solution by weight and the capsicum oleoresin is added to the aqueous solution and stirred until dispersed. The chitosan chloride is dissolved in sufficient water to give 0.3% aqueous solution by weight, and calcium chloride is dissolved in the same solution to give 300 mM solution.

Microcapsules of sodium alginate are formed by dropping drips of alginate capsaicin solution/suspension into the chitosan/calcium chloride solution. The capsules are concentrated such that on shaking the bottle a 5 ml spoonful can be dispensed so that it will contain one dose of capsaicin. On ingesting one 5 ml spoonful the capsules adhere to the oesophagus and stomach mucus lining to provide a slow releasing source of capsaicin for treating gastro-oesophageal reflux disease.

What is claimed is:

1. A pharmaceutical composition for the treatment of gastro-oesophageal reflux disease which comprises
   (1) a carrier vehicle which is capable of producing a floating barrier layer on contact with gastric acid or which is capable of forming a bioadhesive film which binds to the oesophageal region, and
   (2) at least one active ingredient selected from capsaicin ((E)-(N)-[(4-hydroxy-3-methoxyphenyl)-methyl]-8-methyl-6-nonenamide), zingerone (4-(4-hydroxy-3-methoxyphenyl)-2-butanone), curcumin (1,7-bis(4-hydroxy-3-methoxyphenyl)-1,6-heptadiene-3,5-dione), piperine (1-[5-1,3-benzodioxol-5-yl)-1-oxo-2, 4-pentadienyl]-piperidine), resiniferatoxin (daphnetoxin 6,7-deepoxy-6,7-didehydro-5-deoxy-21-dephenyl-21-(phenylmethyl)-20-(4-hydroxy-3-methoxybenzene acetate), pharmaceutically acceptable derivatives and salts thereof.

2. A composition as claimed in claim 1, wherein, on contact with gastric acid, the carrier vehicle forms a floating barrier comprising a carbonated raft, mucoadhesive granules, an oil dispersion, or a wax dispersion.

3. A composition as claimed in claim 2, wherein the carrier vehicle includes an alginate.

4. A composition as claimed in claim 2, wherein the carrier vehicle includes cross-linked polyacrylic acid.

5. A composition as claimed in claim 2, wherein the active ingredient is capsaicin.

6. A composition as claimed in claim 2, wherein the active ingredient is resiniferatoxin.

7. A composition as claimed in claim 1 in which the carrier vehicle forms a bioadhesive film in the oesophagus prior to any contact with gastric acid.

8. A composition as claimed in claim 7, wherein the carrier vehicle includes an alginate.

9. A composition as claimed in claim 7, wherein the carrier vehicle includes cross-linked polyacrylic acid.

10. A composition as claimed in claim 7, wherein the active ingredient is capsaicin.

11. A composition as claimed in claim 7, wherein the active ingredient is resiniferatoxin.

12. A composition according to claim 1 in which the active ingredient comprises the crude extracts of capsicum, cayenne pepper, black pepper, paprika, mace, mustard, ginger, turmeric or papaya seed.

13. A composition according to claim 1 which is in unit dosage form and comprises from 0.001 to 40 mg of active ingredient.

14. A composition according to claim 13 in which the unit dosage form comprises from 0.025 to 2.5 mg of the active ingredient.

15. A composition as claimed in claim 14 in which the active ingredient is capsaicin.

16. A method for treating gastro-oesophageal reflux diseases which comprises administering to a person in need of such treatment a composition which comprises
    (1) a carrier vehicle which is capable of producing a floating barrier layer on contact with gastric acid or which is capable of forming a bioadhesive film which binds to the oesophageal region, and
    (2) at least one active ingredient selected from capsaicin ((E)-(N)-[(4-hydroxy-3-methoxyphenyl)-methyl]-8-methyl-6-nonenamide), zingerone (4-(4-hydroxy-3-methoxyphenyl)-2-butanone), curcumin (1,7-bis(4-hydroxy-3-methoxyphenyl)-1,6-heptadiene-3,5-dione), piperine (1-[5-1,3-benzodioxol-5-yl)-1-oxo-2,4-pentadienyl]-piperidine), resiniferatoxin (daphnetoxin 6,7-deepoxy-6,7-didehydro-5-deoxy-21-dephenyl-21-(phenylmethyl)-20-(4-hydroxy-3-methoxybenzene acetate), pharmaceutically acceptable derivatives and salts thereof.

17. A method as claimed in claim 16 in which the carrier vehicle includes an alginate.

18. A method as claimed in claim 16 in which the active ingredient is capsaicin.

19. A method as claimed in claim 16 in which the carrier vehicle forms, on contact with gastric acid, a floating barrier comprising a carbonated raft, mucoadhesive granules, an oily dispersion or a wax dispersion.

20. A method as claimed in claim 16 in which the carrier vehicle forms a bioadhesive film in the oesophagus prior to any contact with gastric acid.

21. In the preparation of medicaments for the treatment of gastric ulcers and/or gastritis, the improvement which comprises incorporating into said medicament a composition which comprises
    (1) a carrier vehicle which is capable of producing a floating barrier layer on contact with gastric acid or which is capable of forming a bioadhesive film which binds to the oesophageal region, and
    (2) at least one active ingredient selected from capsaicin ((E)-(N)-[(4-hydroxy-3-methoxyphenyl)-methyl]-8-methyl-6-nonenamide), zingerone (4-(4-hydroxy-3-methoxyphenyl)-2-butanone), curcumin (1,7-bis(4-hydroxy-3-methoxyphenyl)-1,6-heptadiene-3,5-dione), piperine (1-[5-1,3-benzodioxol-5-yl)-1-oxo-2,4-pentadienyl]-piperidine), resiniferatoxin (daphnetoxin 6,7-deepoxy-6,7-didehydro-5-deoxy-21-dephenyl-21-(phenylmethyl)-20-(4-hydroxy-3-methoxybenzene acetate), pharmaceutically acceptable derivatives and salts thereof.

22. The improvement as claimed in claim 21 in which the active ingredient is capsaicin.

23. The improvement as claimed in claim 21 in which the carrier vehicle comprises alginate.

\* \* \* \* \*